(12) United States Patent
Guaino

(10) Patent No.: US 10,283,420 B2
(45) Date of Patent: May 7, 2019

(54) METHOD FOR THE PRODUCTION OF AN OPTOELECTRONIC MODULE INCLUDING A SUPPORT COMPRISING A METAL SUBSTRATE, A DIELECTRIC COATING AND A CONDUCTIVE LAYER

(71) Applicant: ArcelorMittal, Luxembourg (LU)

(72) Inventor: Philippe Guaino, Liège (BE)

(73) Assignee: ArcelorMittal, Luxembourg (LU)

( * ) Notice: Subject to any disclaimer, the term of this patent is extended or adjusted under 35 U.S.C. 154(b) by 38 days.

(21) Appl. No.: 15/537,662

(22) PCT Filed: Dec. 23, 2015

(86) PCT No.: PCT/IB2015/059922
§ 371 (c)(1),
(2) Date: Jun. 19, 2017

(87) PCT Pub. No.: WO2016/103206
PCT Pub. Date: Jun. 30, 2016

(65) Prior Publication Data
US 2018/0005905 A1    Jan. 4, 2018

(30) Foreign Application Priority Data

Dec. 24, 2014 (WO) .................. PCT/IB2014/067309

(51) Int. Cl.
*H01L 21/66* (2006.01)
*G01N 25/72* (2006.01)
(Continued)

(52) U.S. Cl.
CPC ................ *H01L 22/12* (2013.01); *G01J 5/10* (2013.01); *G01N 25/72* (2013.01); *H01L 22/14* (2013.01);
(Continued)

(58) Field of Classification Search
CPC .................. H01L 31/18; H01L 31/0216; H01L 31/02002; G01J 5/10; G01J 5/12;
(Continued)

(56) References Cited

U.S. PATENT DOCUMENTS 6,317,216 B1 * 11/2001 Maris ................ G01N 21/8422
257/E21.53
7,651,874 B2 * 1/2010 Nagel ................ G01N 21/6489
257/E21.521
(Continued)

FOREIGN PATENT DOCUMENTS

EP    2320473 A1    5/2011
EP    2925089 A1    9/2015
(Continued)

OTHER PUBLICATIONS

Jun Xia, "Development of Deep-Level Photo-Thermal Spectroscopy and Photo-Carrier Radiometry for the Characterization of Semi-Insulating Gallium Arsenide," University of Toronto (Year: 2010).*
(Continued)

*Primary Examiner* — Maliheh Malek
(74) *Attorney, Agent, or Firm* — Davidson, Davidson & Kappel, LLC

(57) ABSTRACT

The invention is directed to a method for the production of an optoelectronic module including a support (5) and an additional layer, said support being formed by an assembly (25) which has no optoelectronic properties and which comprises, successively, a metal substrate (27), a dielectric coating (29) disposed on the metal substrate, and an electrically conductive layer (31) disposed on the dielectric coating. The production method comprises: a step of providing the support and performing a method in which the support is checked, or providing the support after it has already been checked; and a step of depositing at least one
(Continued)

additional layer on the electrically conductive layer. The method in which support is checked comprises the following steps: electrical excitation of the support by bringing the metal substrate and the electrically conductive layer into electrical contact with a voltage source (33); and photothermal examination of the excited support so as to detect any possible fault (49, 51) located at least partially in the dielectric coating (29) and to provide a photothermal examination result.

18 Claims, 1 Drawing Sheet

(51) Int. Cl.
<table>
<tr><td>G01J 5/10</td><td>(2006.01)</td></tr>
<tr><td>H01L 31/0216</td><td>(2014.01)</td></tr>
<tr><td>H02S 50/10</td><td>(2014.01)</td></tr>
<tr><td>H01L 31/18</td><td>(2006.01)</td></tr>
<tr><td>H01L 31/02</td><td>(2006.01)</td></tr>
<tr><td>G01J 5/00</td><td>(2006.01)</td></tr>
</table>

(52) U.S. Cl.
CPC .... *H01L 31/02002* (2013.01); *H01L 31/0216* (2013.01); *H01L 31/18* (2013.01); *H02S 50/10* (2014.12); *G01J 2005/0077* (2013.01)

(58) Field of Classification Search
CPC ...... G01J 5/20; G01J 5/28; G01J 5/505; G01J 5/54; G01J 5/56; G01J 2005/0077; G01J 2005/103; G01J 2005/283; G01J 2005/286; G01N 25/72; H02S 50/10; H02S 50/15
See application file for complete search history.

(56) References Cited

U.S. PATENT DOCUMENTS

| | | | | |
|---|---|---|---|---|
| 7,910,822 B1* | 3/2011 | Funcell | ............... | H01L 31/18 136/244 |
| 7,979,969 B2 | 7/2011 | Basol | | |
| 7,989,729 B1* | 8/2011 | Zhao | ............... | G01J 1/08 136/244 |
| 8,300,227 B2* | 10/2012 | Chism, II | ............... | G01N 21/55 356/445 |
| 8,462,350 B2* | 6/2013 | Pfaff | ............... | G01B 11/2441 356/503 |
| 8,698,083 B2* | 4/2014 | Fuyuki | ............... | H01L 31/186 250/338.1 |
| 8,710,860 B2* | 4/2014 | Trupke | ............... | G01N 21/6489 324/761.01 |
| 8,766,192 B2* | 7/2014 | Wang | ............... | G01N 25/72 250/341.1 |
| 9,806,672 B2* | 10/2017 | Suthues | ............... | H01L 31/186 |
| 2002/0059035 A1* | 5/2002 | Yagi | ............... | H02S 50/10 702/59 |
| 2005/0252545 A1* | 11/2005 | Nowlan | ............... | G01N 25/72 136/243 |
| 2007/0075050 A1* | 4/2007 | Heyl | ............... | B23K 26/03 219/121.6 |
| 2009/0127448 A1* | 5/2009 | Fuyuki | ............... | H02S 50/10 250/238 |
| 2009/0238444 A1* | 9/2009 | Su | ............... | G01M 11/00 382/149 |
| 2010/0210040 A1 | 8/2010 | Basol | | |
| 2011/0135187 A1 | 6/2011 | Yamamuro | | |
| 2011/0268344 A1* | 11/2011 | Chan | ............... | G01N 21/9505 382/145 |
| 2011/0282600 A1* | 11/2011 | Roesner | ............... | H02S 50/10 702/60 |
| 2012/0018829 A1* | 1/2012 | Beck | ............... | G01J 3/02 257/431 |
| 2012/0113415 A1* | 5/2012 | Haunschild | ............... | H02S 50/10 356/213 |
| 2013/0015875 A1* | 1/2013 | Kumar | ............... | H02S 50/10 324/761.01 |
| 2013/0095577 A1* | 4/2013 | Milshtein | ............... | G01B 11/0683 438/7 |
| 2013/0146576 A1* | 6/2013 | Khan | ............... | H05B 1/00 219/201 |
| 2014/0043056 A1* | 2/2014 | Baba | ............... | G01N 21/6489 324/761.01 |
| 2014/0062500 A1* | 3/2014 | Behrends | ............... | G01R 31/024 324/537 |
| 2014/0093985 A1* | 4/2014 | Li | ............... | H01L 22/12 438/7 |
| 2014/0139260 A1* | 5/2014 | Shankar | ............... | H02S 50/00 324/764.01 |
| 2014/0183366 A1* | 7/2014 | Cole | ............... | G01J 5/20 250/349 |
| 2014/0256068 A1* | 9/2014 | Franklin | ............... | H01L 22/12 438/16 |
| 2014/0266288 A1* | 9/2014 | Trabacchin | ............... | H02S 50/10 324/761.01 |
| 2014/0273313 A1* | 9/2014 | Kumar | ............... | G01N 21/6456 438/16 |
| 2014/0370623 A1* | 12/2014 | Wu | ............... | H01L 31/18 438/5 |
| 2015/0042980 A1* | 2/2015 | Liu | ............... | G01N 21/95 356/51 |
| 2015/0122789 A1* | 5/2015 | Gloeckler | ............... | H05B 1/00 219/201 |
| 2015/0162872 A1* | 6/2015 | Nakanishi | ............... | H02S 50/15 324/761.01 |
| 2015/0222228 A1* | 8/2015 | Zara | ............... | H02S 50/10 324/750.03 |
| 2015/0236642 A1* | 8/2015 | Nakanishi | ............... | H02S 50/15 356/237.1 |
| 2015/0333693 A1* | 11/2015 | Suthues | ............... | H01L 31/186 324/761.01 |
| 2016/0158890 A1* | 6/2016 | Gonzalez | ............... | H01L 22/26 438/5 |
| 2017/0349279 A1* | 12/2017 | Garcia-Gabin | ....... | B64C 39/024 |

FOREIGN PATENT DOCUMENTS

| | | |
|---|---|---|
| JP | 2014107053 | 6/2014 |
| WO | 0107901 A1 | 2/2001 |
| WO | 2011135195 A1 | 11/2011 |
| WO | 2014032781 A1 | 3/2014 |

OTHER PUBLICATIONS

International Search Report Issued in connection with International Application No. PCT/IB2015/059922, dated Mar. 2, 2016.

* cited by examiner

METHOD FOR THE PRODUCTION OF AN OPTOELECTRONIC MODULE INCLUDING A SUPPORT COMPRISING A METAL SUBSTRATE, A DIELECTRIC COATING AND A CONDUCTIVE LAYER

BACKGROUND OF THE INVENTION

Field of the Invention

The present invention is directed to a method for manufacturing an optoelectronic module comprising a support comprising a metal substrate, a dielectric coating, and a conductive layer.

Such a support is, for example, used as a support for powering optoelectronic devices and is particularly suitable for integration in organic or inorganic devices.

Description of Related Art

The relevant optoelectronic devices include components added on the support, such as for example, light-emitting diodes (LEDs), organic light-emitting diodes (OLEDs), photovoltaic cells either in thin layers or not, transistors for viewing screens such as TFT («thin-film transistor») screens or further photosensitive sensors.

Such supports are for example described in document WO 2011/135195 of the applicant, the contents of which are incorporated herein by reference.

The quality of the support notably depends on the integrity of the dielectric coating. In order to test this integrity, according to a first method discussed on page 11 of the aforementioned document, the support is tested in an intermediate manufacturing state, in which it only includes the metal substrate and the dielectric coating. Square conductive pads of a predefined size are deposited in the laboratory on the dielectric coating and a voltage of ten volts is applied on the metal substrate and each pad. Next, the leakage current is measured and the electric insulation at the pad is estimated to be satisfactory if the measured leakage current is less than a certain value in $mA/cm^2$. The electric insulation of the assembly is estimated to be satisfactory when all the pads have a leakage current less than this value.

However, the method does not give the possibility of controlling online the support comprising the metal substrate, the dielectric coating, and the conductive layer, in particular when the latter is continuous over the whole of the support. Further, the method does not give the possibility of testing the dielectric coating located between the pads and beyond the pads. Finally, it does not give the possibility of localizing defects located under a same pad, or either of characterizing them.

On page 12 of the aforementioned document, another monitoring method consists of applying a high voltage to the support and to verify that no breakdown of the dielectric coating occurs by measuring the leakage current. If the leakage current remains less than a certain value, the breakdown voltage of the support is estimated to be sufficiently high.

However, the method does not give the possibility of localizing, or of characterizing the possible defects of the dielectric coating having caused the breakdown.

Moreover, it is known how to control the optoelectronic device obtained from the support. However, such a control occurs at a belated stage of the manufacturing of the optoelectronic device. If the test reveals a defect of the optoelectronic device, this defect may concern just as well the support and subsequently deposited layers or components on the support. In any case, the defect is discovered at a belated stage of the manufacturing. This will cause overcosts.

An object of the invention is therefore to provide a method for manufacturing an optoelectronic module including a control of the support consisting of an assembly successively comprising the metal substrate, the dielectric coating, and the conductive layer, while the assembly is without any optoelectronic properties, the control giving the possibility of localizing defects possibly present in the dielectric coating, and at least to a certain extent of characterizing them.

BRIEF SUMMARY OF THE INVENTION

For this purpose, an object of the invention is a method for manufacturing an optoelectronic module comprising a support and an additional layer located on the support, the support consisting of an assembly without any optoelectronic properties, the assembly successively comprising a metal substrate, a dielectric coating located on the metal substrate, and an electrically conductive layer located on the dielectric coating, the manufacturing method including at least:
  a step for providing the support and applying a method for controlling the support, or a first step for providing the support, the support having been subject to the control method, and
  a step for depositing at least the additional layer on the electrically conductive layer of the support in order to obtain the optoelectronic module, the control method of the support including at least the following steps:
  electric excitation of the support by putting into electric contact the metal substrate and the electrically conductive layer with a voltage source, and
  photothermal examination of the excited support in order to detect a possible defect located at least partly in the dielectric coating and providing a result of photothermal examination.

According to certain embodiments, the manufacturing method comprises one or several of the following characteristics, taken individually or according to all the technically possible combinations:
  the dielectric coating has a relative permittivity greater than or equal to 2;
  the electrically conductive layer substantially covers entirely the dielectric coating;
  the provision of the support comprises a sub-step for depositing the electrically conductive layer on at least one portion of the dielectric coating;
  the sub-step for depositing the electrically conductive layer comprises a chemical phase deposition of the electrically conductive layer on the dielectric coating;
  the electrically conductive layer has a thickness comprised between 10 nanometers and 5 µm;
  the electric excitation step has a duration comprised between 0.01 and 10 seconds;
  at the electric excitation step, the voltage source is adapted for having a direct current $i$ circulate through the support;
  the photothermal examination step comprises the shooting, in the infrared domain, of at least one image of the excited support;

the photothermal examination step comprises the shooting of at least two images shifted in time and/or spectrally with respect to each other;

the photothermal examination step comprises the shooting of more than two images shifted in time and/or spectrally with each other;

the photothermal examination of the support comprises the measurement of the temperature variation of the excited support;

the detection of a possible defect is achieved by determination of an extremum of a representative quantity of a thermal gradient observed in the image;

the provided support is running;

the layer is formed by any of several exemplary materials taken from among: Al, Ag, Au, Mo, Na, Cr, $CeCu_6$, $CeSn_3$, alloys SiGe, $Bi_2Te_3$, PbTe, GeTe, alloys MgSiSn, ZnO, $TiO_2$, Pt, RhFe, vanadium oxides, amorphous silicon, and iron oxides;

the optoelectronic module is a photovoltaic cell; and the additional layer has optoelectronic properties.

The invention finally relates to an assembly comprising:

a support consisting of an assembly without any optoelectronic properties, the assembly without any optoelectronic properties successively comprising a metal substrate, a dielectric coating located on the metal substrate, and an electrically conductive layer located on the dielectric coating, and a result of a photothermal examination obtained by a control method as described above.

BRIEF DESCRIPTION OF THE SEVERAL VIEWS OF THE DRAWINGS

The invention will be better understood upon reading the description which follows, only given as an example and made with reference to the appended drawings wherein.

DETAILED DESCRIPTION OF THE INVENTION

Figure 1:
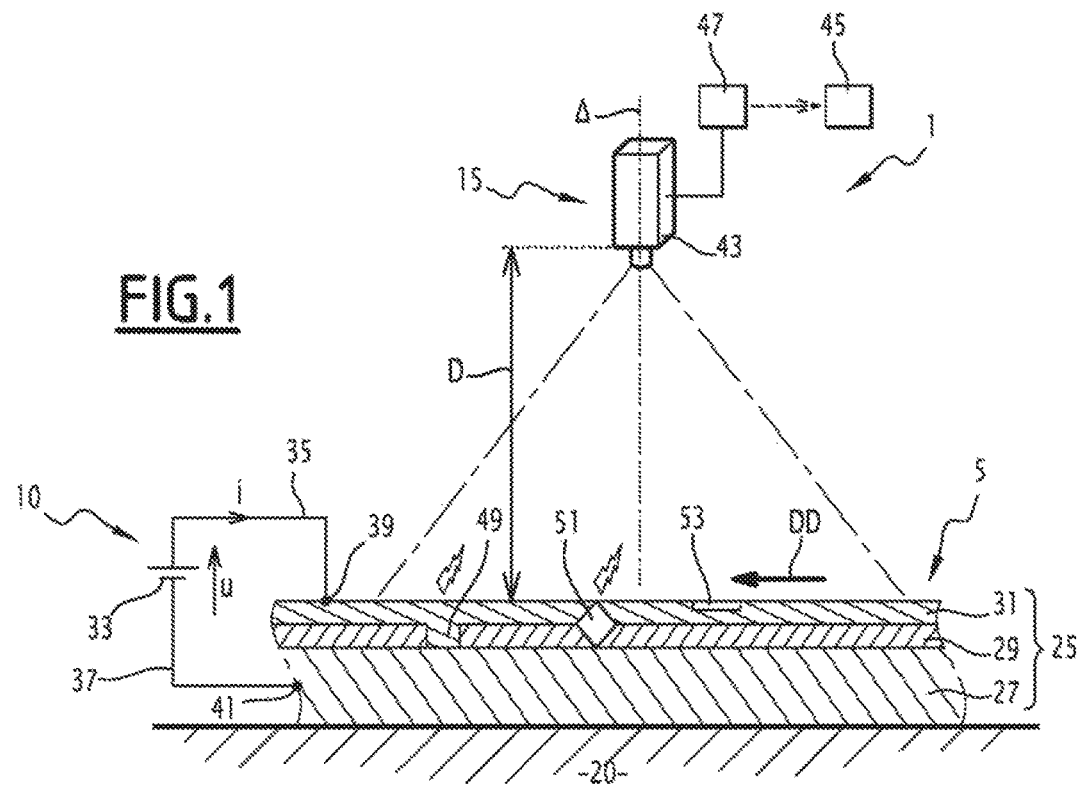
FIG. 1 schematically illustrates an installation adapted for applying steps for providing a support, electric excitation of the support, and photothermal examination of the excited support with a method according to the invention.

With reference to FIG. 1, an installation 1 including a support 5, an electric excitation device 10 for the support 5, and a photothermal examination system 15 for the excited support 5 by the device 10 is described.

The support 5 consists of an assembly 25 without any optoelectronic properties.

By "without any optoelectronic properties", is meant that the assembly 25 does not comprise any optoelectronic component, in other words no electronic component which emits or interacts with light, such as for example light-emitting diodes (LEDs), organic light-emitting diodes (OLEDs), photovoltaic cells in thin layers or not, transistors for viewing screens or further photosensitive sensors.

In the example illustrated in FIG. 1, the assembly 25 successively comprises a metal substrate 27, a dielectric coating 29 located on the metal substrate 27, and an electrically conductive layer 31 located on the dielectric coating 29.

By "electrically conductive layer", is meant a layer having an electric resistivity of less than or equal to $10^{-3}$ ohm·m at room temperature (20° C.).

According to alternatives not shown, the assembly 25 comprises other elements, while remaining without any optoelectronic properties.

The metal substrate 27 is for example a solid body with a flat shape, i.e. with a small thickness as compared with its other dimensions. The substrate may appear as a plate or a sheet consisting of a single metal material or of a composite assembly. The metal substrate 27 is for example a superposition of several layers of the same material or of different materials, for which at least one is a metal material, this superposition may be achieved by gluing, welding, by hot galvanization, by electrogalvanization, by deposition in vacuo.

Preferably, the metal material is a metal alloy such as steel. Depending on the application and on the required performances, it is possible to resort without this list being exhaustive to non-coated steel, to galvanized steel, to steels covered with a zinc alloy comprising 5% by weight of aluminium (Galfan®), to steels covered with a zinc alloy comprising 55% by weight of aluminium, about 1.5% by weight of Silicon, the remainder consisting of zinc and of inevitable impurities due to the elaboration (Aluzinc®, Galvalume®), to steels covered with an Aluminium alloy comprising from 8 to 11% by weight of Silicon and from 2 to 4% by weight of iron, the remainder consisting of aluminium and of inevitable impurities due to the elaboration (Alusi®), to steels covered with an Aluminium layer (Alupur®), to stainless steels.

Still preferably, the metal material métallique is a metal sheet, in other words a flat product obtained by rolling of slabs. In the case of a steel metal sheet, it is possible to resort to products from the list above. Such a metal sheet has a thickness generally comprised between 0.1 mm and 3.0 mm, preferably between 0.3 and 1.5 mm. Such a metal sheet has the advantages of being able to be shaped, notably by profiling, and being able to resist to significant loads, notably as a roof panel.

The dielectric coating 29 has a function of allowing electric insulation of the metal substrate in order to avoid any passage of current between the conductive layer and the substrate.

This dielectric coating 29 may also have a function of giving the possibility of compensating for the roughness of the metal substrate and of providing a regular surface for the deposition of the upper conductive layer.

Moreover, the dielectric coating 29 may also have a function of forming a protective barrier of the electronic device towards particles and diffusing elements from the metal substrate as well as a protective barrier of the metal substrate towards external contaminations, whether this is steam or oxygen which may oxidize or corrode the metal substrate.

The dielectric coating 29 may be formed with organic and/or inorganic layers.

An inorganic dielectric layer may comprise a material selected from ceramics such as for example cordierite, forsterite or steatite or from non-conductive metal oxides such as for example, $TiO_2$, $Al_2O_3$, $SiO_2$, optionally doped with boron or phosphorus. This inorganic dielectric layer may be applied at least partly on the substrate, optionally coated, by means of any known method for depositing thin layers in vacuo.

An organic dielectric layer may for example comprise a polymeric material selected from among thermoplastic polymers or thermosetting polymers, elastomers, polyimides, epoxies, polyolefins, polyamides, cellulose materials, styrene materials, polyacrylic materials, such as methyl polymethacrylate, polyethers, saturated polyesters, vinyl materials, such as vinyl polyacetate, poly-sulfonic materials, fluorinated polymers, organo-inorganic hybrid lacquers based on the sol-gel technique. This organic dielectric layer may be applied at least partly on the substrate, optionally coated, by means of a known method for depositing thin layers.

The dielectric coating for smoothing may advantageously be formed by alternate deposition of any number of organic dielectric layers and of inorganic dielectric layers.

Depending on the number of dielectric layers, the dielectric smoothing coating may have a thickness varying between 500 nm and 50 μm.

Preferably, the dielectric coating 29 has a relative permittivity greater than or equal to 2. According to certain embodiments, the relative permittivity is greater than 5, 10, 100, or even greater than 1,000.

The electrically conductive layer 31 has a primary function of allowing the electric power supply of the electronic devices intended to be placed in contact with all or part of this layer.

For this purpose, the layer 31 has a resistance per square of at least 10Ω, preferably less than 5Ω or less than 1Ω; more preferentially, it has a resistance per square of at most 0.1Ω. Conventionally, by resistance value per square is meant the value of the resistance between two opposite sides of an imaginary square formed on the surface of the layer the resistance of which is measured.

The layer 31 for example comprises one or several metals or metal alloys and/or one or several oxides, nitrides or metal carbides naturally conductive or made to be conductive by addition of conductive elements such as graphite, for example. For example it may comprise an element selected from among the group consisting of Ag, Al, Au, Mo, Na and Cr, these elements being usually used as an electrode in optoelectronic devices. It may itself consist of several sub-layers. It may be applied by means of a method for depositing thin layers in vacuo.

However, these materials are not necessarily the best candidates for increasing the thermoelectric yield (variation of the temperature according to the current which crosses the defect). Indeed, all these materials do not have positive and high temperature coefficients (TCR) and are not good materials with a thermoelectric effect.

A good thermoelectric material is defined by means of its Seebeck coefficient (in $V \cdot K^{-1}$), its electric resistivity $\rho$ (in ohm·cm), its thermal conductivity (in $W \cdot m^{-1} \cdot K^{-1}$). Good thermoelectric materials are found from among the intermetallic alloys, for example $CeCu_6$, $CeSn_3$, SiGe alloys, semi-conductors of the $Bi_2Te_3$, PbTe, GeTe type, MgSiSn alloys, oxides ZnO, $TiO_2$ . . . , and in derived compounds.

Advantageously, the layer 31 is in a material with a positive temperature coefficient (PTC). Such materials have the capability of having a strong positive dependence (increase in the temperature) on their resistivity with temperature. Metals like Pt, RhFe, as well as semi-conductors such as vanadium oxides, amorphous silicon, and iron oxides are good examples of materials with a positive temperature coefficient.

The thickness of the conductive layer 31 is preferably located in the range 10 nm-5 μm for giving the possibility of transferring sufficient electric power depending on the relevant electronic device. In addition to the fact of providing a high conductivity to the coated substrate, the conductive layer, when it is not transparent, may give the possibility of attaining high reflectivity values of at least 90%, preferably of at least 92 or 95%, more preferentially of at least 96 or 97%. This property is of particular interest when the support according to the invention is used for supplying with power a device including a light source such as a light-emitting diode, since it gives the possibility of optimizing the energy yield of the electronic device.

Preferably, the electrically conductive layer 31 substantially covers entirely the dielectric coating 29. By this, is meant that the layer 31 was deposited so as to continuously cover the dielectric coating 29, but it was able to be structured for preparing the future integration of optoelectronic layers. This structuration may have been accomplished during the deposition of the layer 31, for example by means of a set of masks (templates), or after the deposition, for example by laser ablation.

Alternatively, in order to increase the emissivity of the material, the conductive layer 31 of a black coating with strong surface emissivity for example greater than 0.97 is covered, in order to improve the measurement of the temperature contrast.

The electric excitation device 10 comprises a voltage source 33, a first circuit 35 intended to be electrically connected to the layer 31 and the voltage source 33, and a second circuit 37 intended to electrically connect the metal substrate 27 and the voltage source 33.

The first circuit 35 and the second circuit 37 comprise at their end opposite to the voltage source 33 respectively connectors 39, 41 intended to be put into electric contact with the layer 31 and the metal substrate 27, respectively.

The connectors 39, 41 are advantageously adapted for respectively sliding on the layer 31 and the metal substrate 27 when the support 5 runs relatively to the photothermal examination system 15.

The voltage source 33 is advantageously adapted so as to circulate a direct current i through the support 5. For example, the voltage source 33 delivers a direct voltage comprised between 10 mV and 100 V, preferably comprised between 1 and 20 V.

The photothermal examination system 15 comprises a camera 43 adapted for producing at least one image 45 (FIG. 2) of a portion of the support 5 as seen from the side of the electrically conductive layer 31. The system 15 advantageously comprises computer means 47 able to generate the image 45. Advantageously, the means 47 are also adapted for producing calculations from data contained in the image 45.

The photothermal examination system 15 is substantially positioned at the vertical of the area of the support 5 put into electric contact with the voltage source 33.

The camera 43 is for example sensitive to infrared light between 1.5 μm and 14 μm. The camera 43 for example has an optical axis Δ substantially perpendicular to the support 5. The camera 43 is for example a CCD camera.

The camera 43 is advantageously placed at a distance D from the support 5 along the Δ axis comprised between 1 and 100 mm according to the advantageous selection of the optical focussing system. The camera 43 is advantageously configured for producing an image 45 for which the resolution is less than or equal to 5 μm/pixel, preferably less than or equal to 15 μm/pixel, 30 μm/pixel.

The spatial resolution increases when the distance D decreases.

Optionally, the installation 1 comprises a running system 20 adapted for having the support 5 run relatively to the photothermal examination system 15. This running system may correspond to a pre-existing driving system on the line and/or include additional elements, such as an inspection table, a rail for translating the camera, for example in a direction perpendicular to the running direction of the support.

The running system 20 is adapted for having the support 5 run along a direction DD. The direction DD is advantageously substantially perpendicular to the optical axis Δ.

The running system 20 is adapted for unwinding the support 5.

Figure 2:
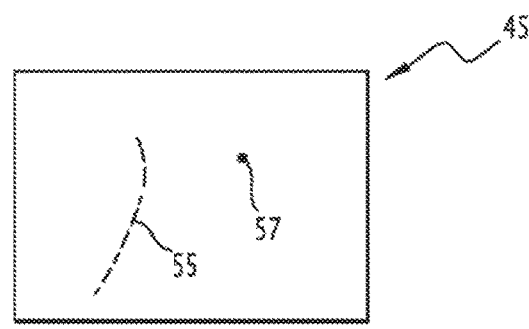
FIG. 2 is a schematic illustration of an image of the excited support, the image being obtained by means of the installation illustrated in FIG. 1, and FIG. 3 schematically illustrates an optoelectronic module obtained by a manufacturing method according to the invention, from the support illustrated in FIG. 1.

With reference to FIGS. 1 and 2, the operation of the installation 1 and a method according to the invention will now be described.

The method comprises at least a step for providing the support 5, a electric excitation step for the provided support, and a photothermal examination step of the excited support for detecting possible defects 49, 51 of insulation of the dielectric coating 29, located at least partly in the dielectric coating 29 and providing a photothermal examination result.

The step for providing the support 5 may comprise the supply of a support 5 manufactured beforehand. In this case, the support may be provided as a coil, be unwound at the inlet of the installation 1, run in the installation by means of the running system, and then be rewound at the outlet of the installation 1.

Alternatively, the support 5 may be at least partly manufactured during the first step of the method according to the invention. In this case, the step for providing the support 5 may comprise a sub-step for depositing the electrically conductive layer 31 on at least one portion of the dielectric coating 29, optionally preceded with a sub-step for depositing the dielectric layer 29 on the metal substrate 27.

Advantageously, the sub-step for depositing the electrically conductive layer 31 is achieved by a chemical phase deposition, such as for example magnetron sputtering, evaporation in vacuo, evaporation by an electron beam in the vapor phase. In this case, the metal substrate 27 may be provided as a coil, be unwound at the inlet of a line for chemical phase deposition, run in the line, and then run in the installation 1 by means of the running system and then be rewound at the outlet of the installation 1.

This alternative has the advantage of allowing the deposition of the electrically conductive layer in all the pores of the dielectric coating, whether these pores are of a micrometric or nanometric size. Accordingly, the detection of the defects is carried out with a very high resolution level, a level not imparted by the other layer deposition techniques.

This alternative also has the advantage of integrating all the steps on a same production line, both on the steps for manufacturing successive layers and the control steps.

The thereby manufactured support 5 is for example in a wound form.

The running system 20 unwinds the support 5. And then the support 5 runs along the direction DD.

The electric excitation step is accomplished by putting into electric contact the metal substrate 27 and the layer 31 with the voltage source 33. In practice, the connectors 39, 41 are put into electric contact respectively with the layer 31 and the metal substrate 27.

The voltage source 33 delivers a voltage U advantageously comprised between 10 mV and 100 V, preferably comprised between 1 and 20V. One skilled in the art will be able to adjust the voltage U depending on the circumstances and in particular depending on the material used for the electrode, on the thickness of the layers, on the size of the defects, etc., so as to avoid degradation of the assembly 25.

The electric excitation step has a duration for example comprised between 0.01 and 10 seconds.

In the case of presence of defects 49, 51, the current i circulates in the support 5 by concentrating on the defects 49, 51. Indeed, the remainder of the dielectric coating 29 behaves like an electric insulator. Localized heating occurs at the defects 49, 51. The layer 31 has a higher surface temperature than at the defect level 49, 51.

The detection and the analysis of the temperature heatings thereby give the possibility of locating and of discriminating the defects.

According to certain embodiments, at least three measuring methods may be contemplated: a continuous method, a pulsed method and an AC method (alternating current) in synchronous detection.

In the continuous method, a direct voltage source (DC) is applied for circulating the direct current, determined by the resistance of the measured defect. The temperature variation $\Delta T$ is measured. The electric excitation step and the photothermal examination step are then concomitant.

In the pulsed method, a voltage pulse is applied for a determined short time. The temperature variation $\Delta T$ is measured after the passing of a current peak through the defect. The photothermal examination step is then successive at the electric excitation step.

In the AC method in synchronous detection, a small alternative variation of the voltage is applied around a determined direct voltage signal. By means of synchronous detection, the alternative $\Delta T$ temperature variation is measured of the emitted signal, and the phase shift relatively to the input signal.

In practice, the measurement of the temperature variation $\Delta T$ is ensured by the photothermal examination system 15.

At the photothermal examination step, at least one image 45 of the excited support 5 is taken in the infrared domain by the camera 43. The higher surface temperature at the defects 49, 51 is thereby detected.

Computer means 47 perform a calculation for obtaining for example a thermal gradient at the surface of the excited support 5, or a quantity representative of this gradient. The means 47 give the possibility of revealing the locations 55, 57 of the image 45 (FIG. 2) where are located the defects 49, 54. For example, the locations 55, 57 are materialized by extremas of the representative quantity.

In the illustrated example, the defect 49 is a dielectric coating scratch 29 materialized by a long trace on the image 45 illustrated in FIG. 2. The defect 51 is a simple inclusion which is expressed by a point on the image 45. It is therefore possible, at least to a certain extent, to discriminate the defects 49, 51.

A defect 53 of the electrically conductive layer 31 is not expressed by any heating and does not appear on the image 45.

According to an alternative, the representative quantity is the temperature, and an extremum of the temperature is sought for revealing the defects 49, 51.

According to an alternative not shown, two images of the excited support 5 are taken, both images being time-shifted and/or spectrally shifted relatively to each other.

In the case of two time-shifted images, this may be for example the same portion of the excited support 5 according to the pulsed method, photographed during two successive pulses. The analysis of these successive images gives the possibility of refining the detection and the characterization of the defects. This may also be two images of two adjacent portions of the excited support taken while the support is running. The computer means 47 give the possibility of juxtaposing the images so as to achieve a mapping of the support.

In the case of two spectrally shifted images, this may for example be the same portion of the excited support photographed in the visible domain on the one hand and in the infrared domain on the other hand. It is then possible to show the defects detected by analysis of the infrared image on the image produced in the visible domain. It is thus possible to establish a mapping of the defects of the support 5.

On the same principle, and according to another alternative not shown, a plurality of images of the excited support 5 are taken, the images being time-shifted and/or spectrally shifted relatively to each other.

The photothermal examination step provides a result of a photothermal examination which for example is the image 45.

Alternatively, the photothermal examination result is a datum according to which the portion of the support 5 corresponding to the image 45 does not have any defects considered as interfering.

At the end of the control method of the support 5, the support 5 estimated to be unsatisfactory or else only the portion corresponding to the image 45, may be rejected.

The support 5 and the photothermal examination result obtained by the aforementioned method form an assembly in which the result of a photothermal examination is advantageously a certificate of the support 5.

Figure 3:
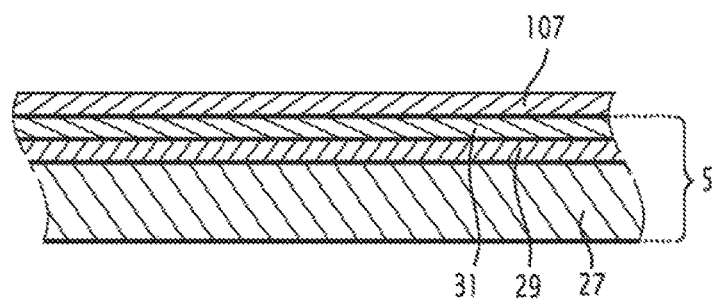

With reference to FIG. 3, an optoelectronic module 100 is described which is for example a photovoltaic cell.

By «photovoltaic cell», is for example meant an electronic component which, exposed to light, produces electricity by the photovoltaic effect.

The optoelectronic module 100 comprises a support 5 similar to the support described above, and an additional layer 107 deposited on the electrically conductive layer 31 of the support 5.

The additional layer 107 has electronic properties in the sense defined above.

The optoelectronic module 100 has photovoltaic properties for which the relevant support 5 alone is without any of them.

For manufacturing the optoelectronic module 100, a control method as described above is applied for testing the support 5.

If the support 5 is estimated to be satisfactory according to the photothermal examination result, the additional layer 107 is deposited on the layer 31 in order to obtain the optoelectronic module 100.

According to an alternative of the manufacturing method, the control method was already applied when the support 5 is provided for manufacturing the optoelectronic module 100. The support 5 used is then an already controlled support, for example on another production site. The support 5 is then advantageously associated with a certificate establishing that the photothermal examination result is correct.

By means of the characteristics described above, the control method of the support 5 gives the possibility of localizing defects 49, 51 possibly located at least partly in the dielectric coating 29, while the support 5 is without any optoelectronic properties. Further, the photothermal examination result gives the possibility, at least to a certain extent, of discriminating between the defects such that for example the point like defect 51, or the deep scratch 49 of the dielectric coating 29.

Although the invention was described for online control, it is obvious that the invention may just as well be applied during quality controls offline, and therefore without any relative displacement of the support relatively to the photothermal examination system.

What is claimed is:

1. A method for manufacturing an optoelectronic module comprising a support and an additional layer located on the support, the support comprising an assembly without any optoelectronic properties, the assembly successively comprising a metal substrate, a dielectric coating located on the metal substrate, and an electrically conductive layer located on the dielectric coating,
    the manufacturing method including at least:
        a step for providing the support and for applying a method for controlling the support, or a step for providing the support, the support having been subject to the method for controlling the support, and
        a step for depositing at least the additional layer on the electrically conductive layer of the support for obtaining the optoelectronic module,
    the method for controlling the support including at least the following steps:
        an electric excitation of the support by putting into electric contact the metal substrate and the electrically conductive layer with a voltage source, and
        a photothermal examination of the excited support for detecting a possible defect located at least partly in the dielectric coating and providing a photothermal examination result.

2. A manufacturing method according to claim 1, wherein the dielectric coating has a relative permittivity greater than or equal to 2.

3. A manufacturing method according to claim 1, wherein the electrically conductive layer substantially covers entirely the dielectric coating.

4. A manufacturing method according to claim 1, wherein the provision of the support comprises a sub-step for depositing the electrically conductive layer on at least one portion of the dielectric coating.

5. A manufacturing method according to claim 4, wherein the sub-step for depositing the electrically conductive layer comprises a physical vapor phase deposition of the electrically conductive layer on the dielectric coating.

6. A manufacturing method according to claim 1, wherein the electrically conductive layer has a thickness comprised between 10 nanometers and 5 µm.

7. A manufacturing method according to claim 1, wherein the electric excitation step has a duration comprised between 0.01 and 10 seconds.

8. A manufacturing method according to claim 1, wherein, in the electric excitation step, the voltage source is adapted for having a direct current $i$ circulate through the support.

9. A manufacturing method according to claim 1, wherein the photothermal examination step comprises the taking, in the infrared domain of at least one image of the excited support.

10. A manufacturing method according to claim 9, wherein the photothermal examination step comprises the taking of at least two time-shifted and/or spectrally-shifted images relatively to each other.

11. A manufacturing method according to claim 10, wherein the photothermal examination step comprises the taking of more than two images time-shifted and/or spectrally-shifted relatively to each other.

12. A manufacturing method according to claim 9, wherein the photothermal examination of the support comprises the measurement of the temperature variation of the excited support.

13. A manufacturing method according to claim 12, wherein the detection of a possible defect is accomplished by determining an extremum of a representative quantity of a thermal gradient observed in the image.

14. A manufacturing method according to claim 1, wherein the provided support is running.

15. A manufacturing method according to claim 1, wherein the layer is formed by one or more materials selected from the group consisting of Al, Ag, Au, Mo, Na, Cr, $CeCu_6$, $CeSn_3$, alloys SiGe, $Bi_2Te_3$, PbTe, GeTe, alloys MgSiSn, ZnO, $TiO_2$, Pt, RhFe, vanadium oxides, amorphous silicon and iron oxides.

16. A manufacturing method according to claim 1, wherein the optoelectronic module is a photovoltaic cell.

17. A manufacturing method according to claim 1, wherein the additional layer has optoelectronic properties.

18. A method for manufacturing an optoelectronic module comprising a support and an additional layer located on the support, the support consisting of an assembly without any optoelectronic properties, the assembly successively comprising a metal substrate, a dielectric coating located on the metal substrate, and an electrically conductive layer located on the dielectric coating, the manufacturing method including at least:
   a step for providing the support and for applying a method for controlling the support, or a step for providing the support, the support having been subject to the method for controlling the support, and
   a step for depositing at least the additional layer on the electrically conductive layer of the support for obtaining the optoelectronic module,
the method for controlling the support including at least the following steps:
   an electric excitation of the support by putting into electric contact the metal substrate and the electrically conductive layer with a voltage source, and
   a photothermal examination of the excited support for detecting a possible defect located at least partly in the dielectric coating and providing a photothermal examination result.

* * * * *